(12) United States Patent
Umemoto (10) Patent No.: US 10,238,554 B2
(45) Date of Patent: Mar. 26, 2019

(54) ABSORBENT PRODUCTS HAVING AN ABSORBER WITH A BODY FLUID INFLOW PORTION AND A SUPERABSORBENT RESIN

(71) Applicant: DAIO PAPER CORPORATION, Shikokuchuo-shi, Ehime (JP)

(72) Inventor: Kaori Umemoto, Sakura (JP)

(73) Assignee: DAIO PAPER CORPORATION, Ehime (JP)

( * ) Notice: Subject to any disclaimer, the term of this patent is extended or adjusted under 35 U.S.C. 154(b) by 286 days.

(21) Appl. No.: 14/901,673

(22) PCT Filed: Jun. 27, 2014

(86) PCT No.: PCT/JP2014/067189
§ 371 (c)(1),
(2) Date: Dec. 28, 2015

(87) PCT Pub. No.: WO2014/208729
PCT Pub. Date: Dec. 31, 2014

(65) Prior Publication Data
US 2016/0143790 A1    May 26, 2016

(30) Foreign Application Priority Data
Jun. 28, 2013   (JP) .................... 2013-137084

(51) Int. Cl.
| A61F 13/15 | (2006.01) |
| A61F 13/20 | (2006.01) |
| A61F 13/532 | (2006.01) |
| A61F 13/534 | (2006.01) |

(Continued)

(52) U.S. Cl.
CPC .......... *A61F 13/5323* (2013.01); *A61F 13/45* (2013.01); *A61F 13/472* (2013.01);
(Continued)

(58) Field of Classification Search
CPC .......... A61F 13/5323; A61F 2013/4587; A61F 2013/53051; A61F 2013/53054; A61F 2013/5315
See application file for complete search history.

(56) References Cited

U.S. PATENT DOCUMENTS 6,099,515 A    8/2000   Sugito
6,459,016 B1 *  10/2002   Rosenfeld ............. A61F 13/533
                                                                428/221

(Continued)

FOREIGN PATENT DOCUMENTS

EP    0 531 714    3/1993
JP    60-97121    7/1985

(Continued)

*Primary Examiner* — Michele M Kidwell
(74) *Attorney, Agent, or Firm* — Norris McLaughlin, P.A.

(57) ABSTRACT

An absorber includes a concave groove-shaped body fluid inflow portion along a longitudinal direction of an incontinence pad and over a range in the longitudinal direction including a body fluid discharge portion of a wearer, and a granular powder superabsorbent resin is arranged at least on a side edge portion of the absorber and over the range in the longitudinal direction including the body fluid inflow portion. Since the body fluid flowing into the body fluid inflow portion is diffused and is absorbed and held in the superabsorbent resin on the side edge portion of the absorber, it is possible to provide an adequate absorbed amount in the absorber despite the concave groove in the absorber. Even when the superabsorbent resin becomes swollen with absorbed body fluid, the body fluid inflow portion is not blocked, with the result that the absorption speed is not reduced.

4 Claims, 7 Drawing Sheets

(51) Int. Cl.
  *A61F 13/472* (2006.01)
  *A61F 13/45* (2006.01)
  *A61F 13/53* (2006.01)
  *A61F 13/531* (2006.01)

(52) U.S. Cl.
  CPC .... *A61F 13/534* (2013.01); *A61F 2013/4587* (2013.01); *A61F 2013/5315* (2013.01); *A61F 2013/53024* (2013.01); *A61F 2013/53051* (2013.01); *A61F 2013/530226* (2013.01); *A61F 2013/530868* (2013.01)

(56) References Cited

U.S. PATENT DOCUMENTS

| | | | | |
|---|---|---|---|---|
| 2008/0167634 A1* | 7/2008 | Kouta | ............... | A61F 13/53409 604/367 |
| 2011/0207147 A1* | 8/2011 | Jewett | ................. | C07D 225/08 435/7.21 |
| 2012/0035566 A1* | 2/2012 | Sagisaka | ............. | A61F 13/4756 604/380 |
| 2012/0220972 A1* | 8/2012 | Kawamura | ....... | A61F 13/49001 604/383 |
| 2014/0163503 A1* | 6/2014 | Arizti | .................. | A61F 13/5323 604/366 |
| 2015/0283002 A1 | 10/2015 | Akiyama | | |

FOREIGN PATENT DOCUMENTS

| | | |
|---|---|---|
| JP | 3012472 | 12/1999 |
| JP | 2000-93457 | 4/2000 |
| JP | 3406214 | 3/2003 |
| JP | 3811000 | 6/2006 |
| JP | 2008-284190 | 11/2008 |
| JP | 2011-120710 | 6/2011 |
| WO | WO-2006/017721 | 2/2006 |

* cited by examiner

ABSORBENT PRODUCTS HAVING AN ABSORBER WITH A BODY FLUID INFLOW PORTION AND A SUPERABSORBENT RESIN

BACKGROUND OF THE INVENTION

The present invention relates to absorbent products, such as an incontinence pad, a sanitary napkin, a panty liner and a disposable diaper for absorbing urine, menstrual blood, vaginal discharge and the like, that include a concave groove-shaped body fluid inflow portion for receiving a large amount of body fluid with an absorber.

Conventionally, as an absorbent product such as an incontinence pad, a sanitary napkin, a panty liner or a disposable diaper, an absorbent product is known in which an absorber formed of cotton-like pulp or the like is interposed between a liquid-impermeable back surface sheet such as a polyethylene sheet or a polyethylene sheet laminated non-woven fabric and a liquid-permeable front surface sheet such as a non-woven fabric or a liquid-permeable plastic sheet.

Among such absorbent products, in the case of an incontinence pad for a large amount in which a setting value for the amount of moisture absorbed exceeds 100 cc, since the incontinence pad needs to receive, at a time, a large amount of urine in a small area of a crotch portion, the incontinence pad is developed in which a concave portion is provided in order to promote the temporary storage of urine in the surface of the absorber and the diffusion thereof.

For example, Japanese Patent No. 3811000 discloses a disposable diaper which includes a liquid-permeable front surface sheet, a liquid-impermeable back surface sheet and an absorbent core interposed between both the sheets, in which the core is coated with an absorption diffusion sheet, in which at least one groove recessed in a direction extending from the surface sheet to the back sheet is formed in the core on the side of the surface sheet, in which the bottom portion and the side wall portion of the groove are covered with the surface sheet, in which the core contains a water-absorbent fiber and superabsorbent resin particles and in which the water-absorbent fiber and the superabsorbent resin particles are interposed between the surface sheet and the back surface sheet in the bottom portion of the groove.

Japanese Patent No. 3406214 discloses a disposable diaper in which along an imaginary line extending in a direction from a front waist region through a crotch region to a back waist region, at least a part of a core is divided, in which the core is formed with one fiber layer mainly made of pulverized pulp and one particle layer mainly made of superabsorbent resin particles, which is a substantially laminate product where the fiber layer is located on the particle layer and in which the particle layer is exposed to the side surface of the core in the divided portion.

Furthermore, Japanese Patent No. 3012472 discloses a disposable diaper in which an absorbent core is interposed between a liquid-permeable front surface sheet and a liquid-impermeable back surface sheet, which is formed, in a forward and backward direction, with a front body, a back body and a crotch region located therebetween and which includes a concave portion capable of storing feces in the crotch region of the core.

SUMMARY OF INVENTION

However, in the disposable diaper disclosed in Japanese Patent No. 3811000, since the superabsorbent resin particles are interposed in the bottom portion of the groove into which body fluid flows, so-called "gel blocking" occurs in which air gaps between the polymer particles swollen at the time of water absorption are extremely shrunken, with the result hat necessary absorption power may not be realized in groove. (The term "water" whenever used hereinbelow is inclusive not on water, which is a convenient liquid for testing, but also other body liquids, namely, urine, blood and other menstrual liquids, all of which are water-containing, i.e., aqueous.) There is a concern that the occurrence of the gel blocking prevents the diffusion from the groove to the surrounding area to lower the absorption speed. On the other hand, in the case of the disposable diaper disclosed in Japanese Patent No. 3406214, since the particle layer is exposed to the side surface of the absorbent core in the divided portion, when a large amount of urine is received in the divided portion, the particle layer is swollen to block the divided region, with the result that the absorption speed may be lowered. Furthermore, in the case of the disposable diaper disclosed in patent literature 3 Japanese Patent No. 3012472, because a concave portion is provided in the absorbent core which reduces the body fluid absorption capacity of the absorbent core accordingly, and no means for compensating for it is provided, there is a concern that the absorbed amount in the absorbent core is lowered.

Hence, a main object of the present invention is to provide an absorbent product in which even when a concave groove-shaped absorber inflow portion is provided in an absorber, the decrease in the absorption speed of body fluid caused by gel blocking is prevented, and thus the absorbed amount in the entire absorbent product can be maintained at a desired level.

In order to solve the problem described above, according to aspect one of the present invention, there is provided an absorbent product in which an absorber is interposed between a liquid-permeable front surface sheet and a back surface sheet, where the absorber includes a concave groove-shaped body fluid inflow portion along a longitudinal direction of the absorbent product and over a range in the longitudinal direction including a body fluid discharge portion, and a powder and granular superabsorbent resin is arranged at least on a side edge portion of the absorber and over the range in the longitudinal direction including the body fluid inflow portion.

In aspect one of the invention, the absorber includes the concave groove-shaped body fluid inflow portion along the longitudinal direction of the absorbent product and over the range in the longitudinal direction including the body fluid discharge portion. The body fluid inflow portion is intended to temporarily store the body fluid and to diffuse it into the absorber when a large amount of body fluid such as urine is discharged at a time, and thus the body fluid inflow portion can receive a large amount of body fluid discharged at a time even when the area of the absorber is small. The body fluid flowing into the body fluid inflow portion is also absorbed by the absorber from the side surface of the body fluid inflow portion, with the result that as compared with a case where the body fluid is absorbed from the surface of an absorber formed in a planar shape, the absorption speed is increased.

Because the body fluid inflow portion is provided in the absorber, the capacity of the absorber is reduced accordingly and thus the absorption capacity of the absorber is lowered if no other measures are taken. However, in the absorbent product of the invention, since the granular powder superabsorbent resin is arranged at least on the side edge portion of the absorber and over the range in the longitudinal direction including the body fluid inflow portion, the body fluid flowing into the body fluid inflow portion is diffused within the absorber and is absorbed and held in the superabsorbent resin on the side edge portion of the absorber, with the result that it is possible to compensate for the absorbed amount in the absorber reduced by the provision of the body fluid inflow portion and it is possible to maintain the absorbed amount in the absorber at a desired level. Moreover, since the superabsorbent resin is intensively provided on the side edge portion of the absorber, even when the superabsorbent resin absorbs water to become swollen, the body fluid inflow portion is prevented from being blocked, with the result that the absorption speed being reduced is prevented.

As aspect two of the present invention, the absorbent product of aspect one is provided where a side non-woven fabric is arranged in each of both side portions on a skin side along the longitudinal direction, and the superabsorbent resin is arranged on a surface of the absorber on the skin side overlapping the side non-woven fabric and over the range in the longitudinal direction including the body fluid inflow portion.

In aspect two of the invention, the superabsorbent resin is arranged on the side edge portion of the absorber and on the surface of the absorber on the skin side overlapping the side non-woven fabric and over the range in the longitudinal direction including the body fluid inflow portion. Specifically, the superabsorbent resin is not arranged on the skin side surface of the absorber in the center portion (the effective absorber width) in the width direction in which the side non-woven fabric is not interposed between the side non-woven fabrics on the left and right sides, and the superabsorbent resin is arranged on the skin side surface of the absorber overlapping the side non-woven fabric. In this way, it is possible to further increase the amount of water absorbed by the entire absorber, and even when the superabsorbent resin arranged on the skin side surface of the absorber absorbs water to become swollen, since the side non-woven fabric is interposed on the front surface side, it is possible to prevent the degradation of a feel on the skin surface such as a grainy feel.

As aspect three of the present invention, the absorbent product according aspect one or two is provided where the superabsorbent resin is arranged on the surface of the absorber on a non-skin side and over the range in the longitudinal direction including the body fluid inflow portion.

In aspect three of the invention, the superabsorbent resin is arranged on the surface of the absorber on the non-skin side and over the range in the longitudinal direction including the body fluid inflow portion, and thus it is possible to further increase the absorption capacity in the absorber.

As aspect four of the present invention, the absorbent product according to any one of aspects one to three is provided where the absorber is surround by the wrapping sheet, and the superabsorbent resin is fixed either to both the absorber and the wrapping sheet or to one of the absorber and the wrapping sheet.

In aspect four of the invention, the superabsorbent resin is fixed either to both the absorber and the wrapping sheet or to one of the absorber and the wrapping sheet, and thus the superabsorbent resin is prevented from being displaced and remains in place along the absorber, with the result that the movement of the body fluid from the absorber to the superabsorbent resin is smoothly performed.

As aspect five of the present invention, the absorbent product according to any one of the first to fourth aspects is provided where the body fluid inflow portion is formed either with an opening through which the absorber is penetrates from the skin side to the non-skin side or with a concave portion that is recessed from the skin side to the non-skin side and that has a bottom.

In aspect five of the invention, a means for forming the body fluid inflow portion is specified, and the body fluid inflow portion may be formed with the opening through which the absorber penetrates from the skin side to the non-skin side or may be formed with the concave portion that is recessed from the skin side to the non-skin side and that has a bottom such as with a lamination structure having a concave portion, a lamination structure of the absorber or the addition of an emboss.

Summarizing what is described above, in the present invention, even when a concave groove-shaped absorber inflow portion is provided in an absorber, the decrease in the absorption speed of body fluid caused by gel blocking is prevented, and thus the absorbed amount in the entire absorbent product maintained at as desired level.

DETAILED DESCRIPTION OF THE INVENTION

Embodiments of the present invention will be described in detail below with reference to drawings.

Figure 1:
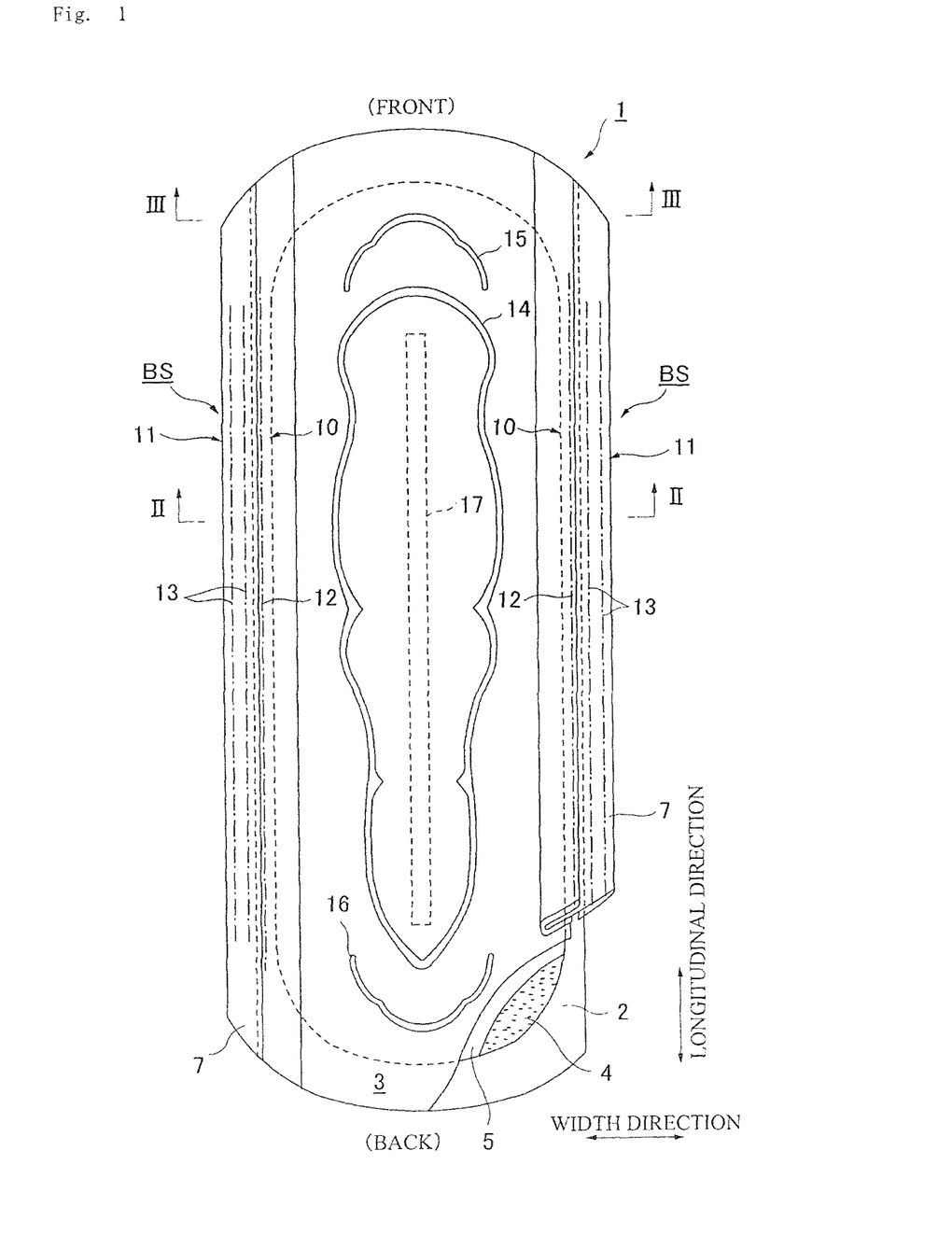
FIG. 1 is a partially broken development view of an incontinence pad 1 according to the present invention.
Figure 2:
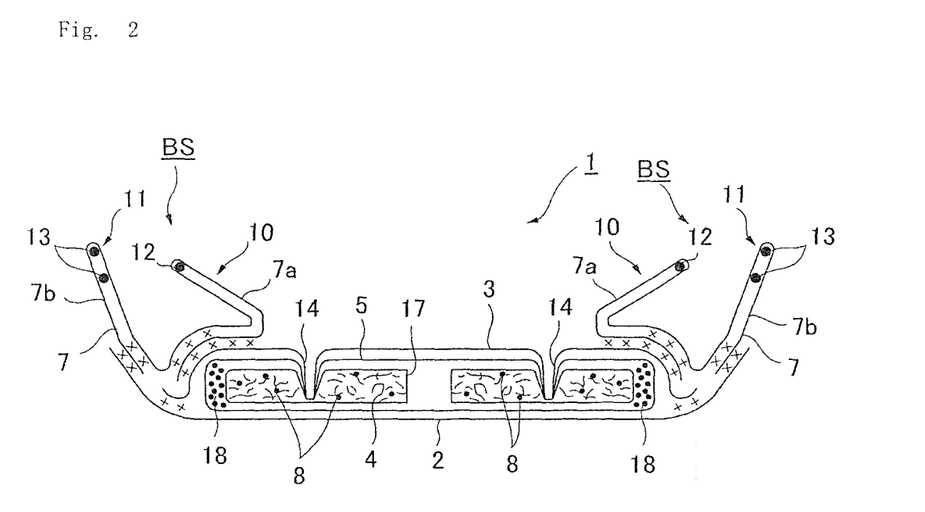
FIG. 2 is a cross-sectional view taken along line II-II of FIG. 1.
Figure 3:
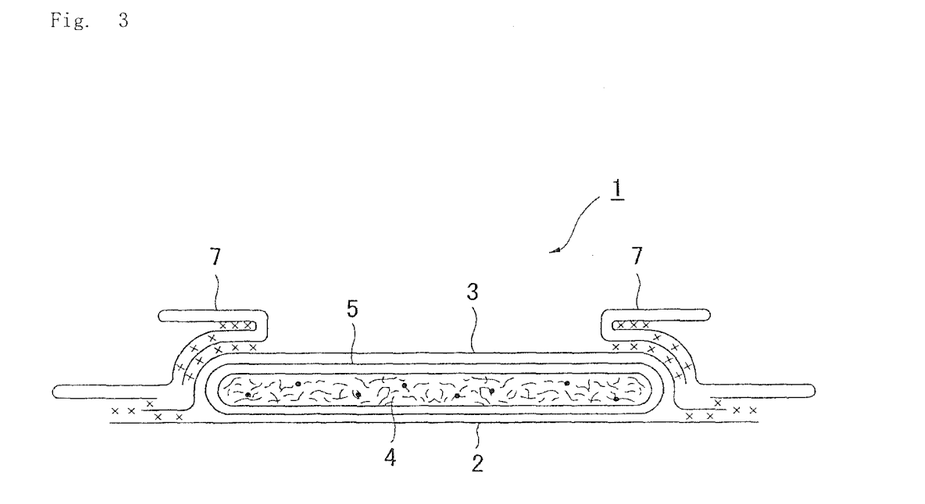
FIG. 3 is a cross-sectional view taken along line III-III of FIG. 1.

As shown in FIGS. 1 to 3, an incontinence pad 1 according to the present invention is mainly formed with: a liquid-impermeable back surface sheet 2 formed from a polyethylene sheet or the like; a liquid-permeable front surface sheet 3 that rapidly transmits urine or other body liquid; an absorber 4 that is interposed between both the sheets 2 and 3 and that is formed of cotton-like pulp, synthetic pulp or the like; a wrapping sheet 5 that surrounds the absorber 4 to hold the shape of the absorber and enhance the diffusivity; and side non-woven fabrics 7 that form a pair of left and right stereoscopic (i.e., three-dimensional) gathers BS which are provided to protrude to a skin side within a predetermined section in a longitudinal direction so as to use a substantial side edge portion of the absorber 4 as a standing base end and to contain at least a body fluid discharge portion. In the surrounding area of the absorber 4, in the end edge portions in the longitudinal direction thereof, the outer edge portions of the liquid-impermeable back surface sheet 2 and the liquid-permeable front surface sheet 3 are joined with an adhesive such as a hot melt or an adhesive means such as a heat seal, and in the both side edge portions, the liquid-impermeable back surface sheet 2 and the side non-woven fabrics 7 extending out laterally beyond the absorber 4 are joined with an adhesive such as a hot melt or an adhesive means such as a heat seal.

The structure of the incontinence pad 1 is described in further detail below. As the liquid-impermeable back surface sheet 2, a sheet material, such as polyethylene or polypropylene, that provides at least aqueous shielding is used; alternatively, a non-woven fabric in which a waterproof film is interposed to provide liquid imperviousness (in this case, the waterproof film and the non-woven fabric constitute the liquid-impermeable back surface sheet) or the like can be used. In recent years, for the purpose of sweatiness prevention, a sheet having moisture permeability has tended to be used. As the aqueous shielding and moisture-permeable sheet material described above, a microporous sheet is preferably used that is obtained by melting and kneading an inorganic filler into an olefin resin such as polyethylene or polypropylene to form a sheet and thereafter stretching the sheet in a uniaxial direction or biaxial directions.

As the liquid-permeable front surface sheet 3, a porous or non-porous non-woven fabric, a porous plastic sheet or the like is preferably used. As the material fiber of the non-woven fabric, for example, a synthetic fiber such as olefin such as polyethylene or polypropylene, polyester or polyamide, a regenerated fiber such as rayon and cupra or a natural fiber such as cotton can be used; a non-woven fabric obtained by an appropriate processing method such as a spun lace method, a spun bond method, a thermal bond method, a melt-blown method or a needle punching method can be used. Among these processing methods, the spun lace method provides non-woven fabric excellent in flexibility and drape and the thermal bond method provides non-woven fabric excellent in bulkiness and compression resilience.

The absorber 4 is formed with, for example, an absorbent fiber such as cotton-like pulp and a superabsorbent resin 8, and in an example shown in the drawings, its planar shape is substantially an ellipse with its major (longer) axis in the longitudinal direction of the absorbent product. The superabsorbent resin 8 is, for example, a granular powder and is dispersed and mixed in the pulp forming the absorber 4. The configuration of the absorber 4 is described in detail hereinbelow.

Examples of the pulp include a chemical pulp obtained from wood, a cellulose fiber such as a dissolving pulp and an artificial cellulose fiber such as rayon and acetate; as compared with a hardwood pulp, a softwood pulp whose fibers are long is preferably used in terms of function and price. As shown in the drawings, when the absorber 4 is surrounded by the wrapping sheet 5, the wrapping sheet 5 is interposed between the liquid-permeable front surface sheet 3 and the absorber 4, with the result that body fluid, such as urine and other body fluids, is rapidly diffused by the wrapping sheet 5 which is excellent in absorption and urine and the body fluid is thereby prevented from returning into contact with the wearer's skin.

Examples of the superabsorbent resin 8 include a cross-linked polyacrylate, a self-crosslinked polyacrylic acid salt, an acrylic acid ester-saponified vinyl acetate copolymer which is cross-linked, an isobutylene-maleic anhydride copolymer which is cross-linked, a cross-linked polysulfone salt and a partially cross-linked water-swellable polymer such as polyethylene oxide or polyacrylamide. Among them, polymers comprising acrylic acid and an acrylic acid salt are preferred because they are excellent in absorbed amount of water and absorption speed. In the superabsorbent resin 8 having the absorption performance described above, in its manufacturing process, a cross-linking density and a cross-linking density gradient are adjusted, and thus it is possible to adjust water absorption power (absorption seating) and water absorption speed.

A synthetic fiber may be mixed with the absorber 4. As the synthetic fiber, for example, polyolefin such as polyethylene or polypropylene, polyester such as polyethylene terephthalate or polybutylene terephthalate, polyamide such as nylon, the copolymers thereof and the like can be used or two types thereof may be mixed and used. Composite fibers such as a sheath/core type fiber in which a high-melting point fiber is used as a core and a low-melting point fiber is used as a sheath, a side-by-side type fiber and a division type fiber can also be used. When the synthetic fiber is a hydrophobic fiber, surface processing is preferably performed with a hydrophilizing agent such that an affinity is provided for body fluid.

The absorber 4 is surrounded by the wrapping sheet 5. Although as the wrapping sheet 5, a paper material such as tissue or a liquid-permeable sheet material such as a non-woven fabric can be used, the fiber density thereof is preferably such a that the pulp and the superabsorbent resin contained in the absorber 4 cannot pass through the wrapping sheet.

In both side portions on the surface side of the incontinence pad 1, the side non-woven fabrics 7 are provided along the longitudinal direction and over the entire length of the incontinence pad 1, and an external part of the side non-woven fabrics 7 is extended laterally and the liquid-impermeable back surface sheet 2 is extended laterally, with the result that the part of the side non-woven fabrics 7 and the part of the liquid-impermeable back surface sheet 2 extended laterally are joined with a hot-melt adhesive or the like to form side flaps.

As the side non-woven fabric 7, either a non-woven fabric, processed to be water repellent or processed to be hydrophilic can be used depending on the function on which importance is placed. For example, when importance is placed on, for example, a function of preventing the penetration of urea or other body fluid or of enhancing a feel, a water-repellent non-woven fabric, such as SSMS (spun-spun-melt-spun), SMS (spun-melt-spun) or SMMS (spun-melt-melt-spun), that is coated with a silicon-based water repellent agent, a paraffin-based water repellent agent or an alkyl chromic chloride-based water repellent agent is preferably used. When importance is placed on the absorption of a body fluid, a hydrophilic non-woven fabric is preferably used in which such as by a method of performing, in a step of manufacturing a synthetic fiber, polymerization in the presence of a compound having a hydrophilic group, for example, an oxidation product of polyethylene glycol or a method of performing processing with a metal salt such as stannic chloride to partially dissolve the surface to provide porosity and depositing a hydroxide of the metal, the synthetic fiber is swollen or is made porous and in which hydrophilicity is provided by the application of capillarity. As the side non-woven fabric 7, a fabric can be used in which a natural fiber, a synthetic fiber or a regenerated fiber is used as a material and which can be formed with an appropriate processing method.

The side non-woven fabrics 7 form the stereoscopic gathers BS of a double gather structure formed with a pair of left and right inner stereoscopic gathers 10 which are folded as necessary and which stand on the skin side with a position near a substantial side edge of the absorber 4 being the standing base end and a pair of left and right outer stereoscopic garners 11 which are located externally with respect to the inner stereoscopic gathers 10, which are formed with the liquid-impermeable back surface sheet 2 and the side non-woven fabrics 7 extended laterally beyond the absorber 4 and which stand on the skin side. Such a double gather structure is adopted, and thus an effect of preventing leakage is enhanced, and as is described in detail hereinbelow, even in a state where a superabsorbent resin 9 provided on the side portion of the absorber 4 absorbs water to become swollen, it is possible to mitigate an unpleasant feel on the skin surface such as a grainy feel. The stereoscopic gathers BS may have a single gather structure formed with only any one of the inner stereoscopic gathers 10 and the outer stereoscopic gathers 11 or only the side non oven fabrics 7 may be provided, that is, the stereoscopic gathers BS may not be formed in the shape of a stereoscopic gather standing on the skin side.

The structure of the inner stereoscopic gathers 10 and the outer stereoscopic gathers 11 are described hereinbelow in detail. In the side non-woven fabrics 7, as shown in FIG. 2, both side ends in the width direction are folded back on the back surface side of the pad to respectively form double sheet portions 7a and 7b on the inner side and the outer side in the width direction; one or a plurality of filamentous resilient and elastic members, in the example shown in the drawings, one filamentous resilient and elastic member 12 in which both ends or an appropriate portion in the longitudinal direction is fixed to the interior of the double sheet portion 7a on the inner side in the width direction is provided; one or a plurality of filamentous resilient and elastic members, in the example shown in the drawings, two filamentous resilient and elastic members 13 in which both ends or an appropriate portion in the longitudinal direction is fixed to the interior of the double sheet portion 7b on the outer side in the width direction are provided; the base end portion of the double sheet portion 7a on the inner side in the width direction is adhered with a hot-melt adhesive or the like to the upper surface of the liquid-permeable front surface sheet 3 provided on the side portion of the absorber 4; the base end portion of the double sheet portion 7b on the outer side in the width direction is adhered with a hot-melt adhesive or the like to the side end portion of the liquid-impermeable back surface sheet 2 extended out laterally beyond the absorber 4; and thus the inner stereoscopic gathers 10 which stand on the skin side with the double sheet portion 7a on the inner side in the width direction are formed and the outer stereoscopic gathers 11 which stand on the skin side with the double sheet portion 7b on the outer side in the width direction are formed. In both end portions of the side non-woven fabrics 7 in the longitudinal direction of the pad, as shown in FIG. 3, the filamentous resilient and elastic members 12 and 13 are not provided, and the double sheet portion 7a on the inner side in the width direction is joined to the side of the absorber 4 with a hot-melt adhesive or the like.

In the incontinence pad 1, as shown in FIG. 1, a center portion emboss 14 which is elongated from the surface side of the liquid-permeable front surface sheet 3 in the longitudinal direction of the pad (i.e., absorbent product) and which is continuously closed as a whole in a circumferential direction, a front side emboss 15 which is located apart from the front side of the center portion emboss 14 and which is formed substantially in the shape of an umbrella (i.e., an arc) and a back side emboss 16 which is located apart from the back side of the center portion emboss 14 and which is formed substantially in the shape of an umbrella (i.e., an arc) are formed. In the center portion emboss 14, the front portion is provided so as to surround a region corresponding to the urination opening portion of a wearer, and the back portion is provided so as to surround a region corresponding to the buttock groove of the wearer.

The configuration of the absorber 4 is described in detail hereinbelow. In the absorber 4, as shown in FIGS. 1 and 2, a concave groove-shaped body fluid inflow portion 17 which is extended along the longitudinal direction of the pad and which is extended over a range in the longitudinal direction including the urination opening portion of the wearer is provided, and a granular powder superabsorbent resin 18 is arranged at least on the side edge portion of the absorber 4 and over a range in the longitudinal direction including the body fluid inflow portion 17. The body fluid inflow portion 17 is intended to temporarily store urine when a large amount of urine is discharged at a time, and to diffuse it into the absorber 4, and thus the body fluid inflow portion 17 can receive a large amount of urine discharged at a time even when the area of the absorber 4 is small. The urine flowing into the body fluid inflow portion 17 is also absorbed by the absorber 4 from the side surface (the cross section of the absorber 4) of the body fluid inflow portion 17, with the result that as compared with an absorber formed in a planar shape, the absorption speed is also advantageously increased.

Because the body fluid inflow portion 17 is provided in the absorber 4, the capacity of the absorber 4 is reduced accordingly and thus the absorption capacity of the absorber 4 is lowered. However, in the incontinence pad 1, since the granular powder superabsorbent resin 18 is arranged at least on the side edge portion of the absorber 4 and over the range in the longitudinal direction including the body fluid inflow portion 17, the body fluid flowing into the body fluid inflow portion 17 is diffused within the absorber 4 and is absorbed and held in the superabsorbent resin 18, resulting in compensation for the absorbed amount in the absorber 4 being reduced by an amount corresponding to the body fluid inflow portion 17 and it is thereby possible to maintain at a desired level the absorbed amount in the absorber 4. Here, since the superabsorbent resin 18 is intensively provided on the side edge portion of the absorber 4, even when the superabsorbent resin absorbs water to become swollen, the body fluid inflow portion 17 is not blocked, with the result that it the absorption speed is not reduced. The superabsorbent resin 18 is intensively provided on the side edge portion of the absorber 4, the skin surface side thereof is covered by the side non-oven fabrics 7, the stereoscopic gathers BS are formed and thus the superabsorbent resin 18 is does not make direct contact with the skin surface, with the result that the wearer does not experience an uncomfortable feel such as a grainy feel. In particular, since in the incontinence pad 1, as shown in FIG. 2, the stereoscopic gathers BS are formed with the double gather consisting of the inner stereoscopic gathers 10 and the outer stereoscopic gathers 11, and in the intermediate portion of the gathers 8 and 9 in the width direction, the region where the superabsorbent resin 18 is arranged is provided, an opportunity for the region where the superabsorbent resin 18 is arranged to make a direct contact with the skin surface is remarkably lowered, with the result that an uncomfortable feel is further avoided.

The body fluid inflow portion 17 is provided, at least on the center line in the longitudinal direction corresponding to the body fluid discharge portion of the wearer, and is formed so as to be equal to or longer than the length in the longitudinal direction corresponding to the body fluid discharge portion of the wearer. In the example shown in FIG. 1, the body fluid inflow portion 17 is continuously provided from the body fluid discharge portion of the wearer to a portion corresponding to the buttock groove in the longitudinal direction of the pad, and is formed within the center portion emboss 14 closed as a whole circumferentially.

Figure 4:
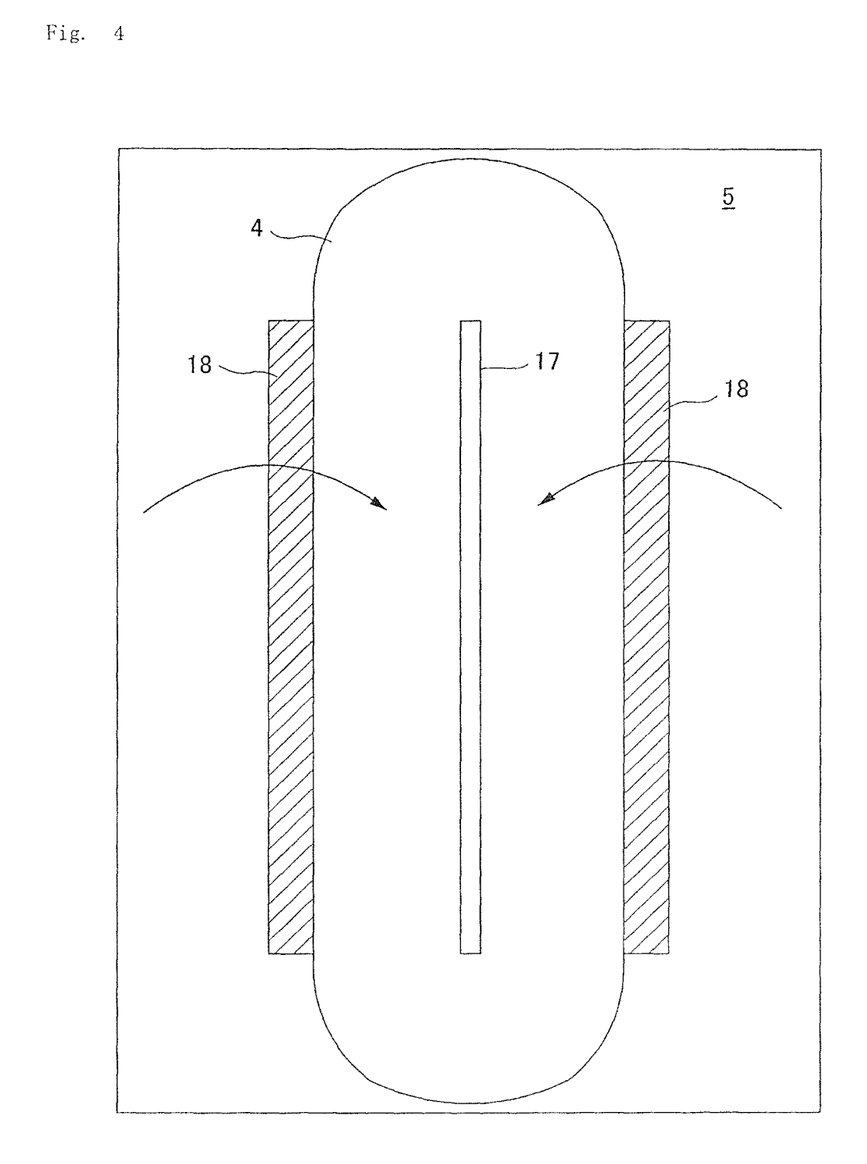
FIG. 4 is a plan view showing a procedure for wrapping an absorber 4 with a wrapping sheet 5.

Preferably, as shown in FIG. 4, the superabsorbent resin 18 arranged on the side edge portion of the absorber 4 is continuously dispersed in the longitudinal direction, has at least a length in the longitudinal direction corresponding to the urination opening portion and is equal to or longer than the length in the longitudinal direction corresponding to the body fluid inflow portion 17. In this way, it is possible to reliably absorb urine flowing into the body fluid inflow portion 17 and diffused in the width direction. However, in order to prevent the degradation of a product cutter when the incontinence pad 1 is cut from a continuous strip in the manufacturing process, the superabsorbent resin 18 is not arranged at either of the front and back end portions of the incontinence pad 1.

Figure 5:
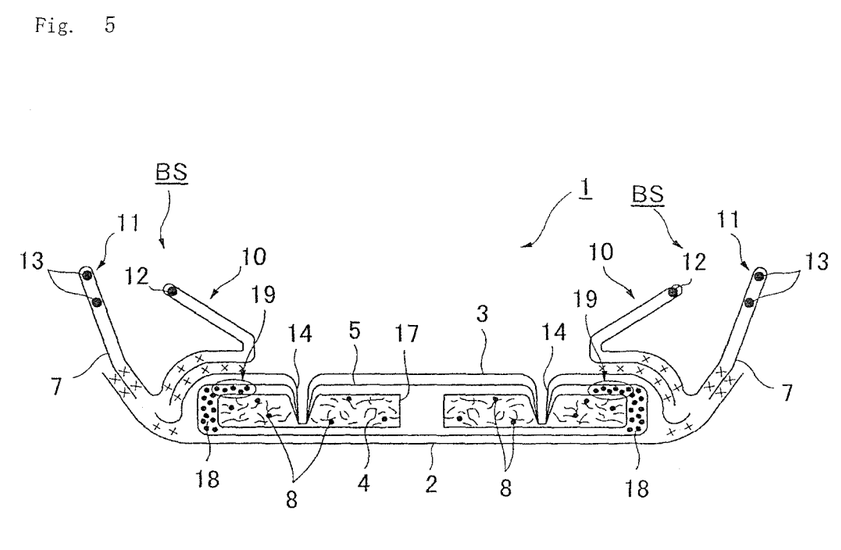
FIG. 5 is a vertical cross-sectional view (arrow view taken along line II-II of FIG. 1) of the incontinence pad 1 showing another embodiment.

As shown in FIG. 5, the superabsorbent resin 18 can be the surface of the absorber 4 on the skin side overlaid on the side non-woven fabrics 7 and can be arranged over the range (range represented by reference numeral 19 in FIG. 5) including the body fluid inflow portion 17. In other words, on the skin side surface of the absorber 4 in the center portion (the width in which the absorber can directly absorb urine: effective absorber width) in the width direction which is between the side non-woven fabrics 7 provided on the left and right sides and in which the side non-woven fabrics 7 are not interposed, the superabsorbent resin 18 is not arranged except when the superabsorbent resin 8 dispersed and mixed with the absorber 4 is present on the surface. In this way, it is possible to increase the amount of water absorbed by the absorber 4, and since in this range 19, the side non-woven fabrics 7 are interposed on the skin side of the absorber 4, even when the superabsorbent resin 18 arranged in this range 19 absorbs water to become swollen, stickiness is unlikely to occur, with the result that in a dried state, an uncomfortable feel such as a grainy feel on the skin surface is avoided. Although the superabsorbent resin 18 arranged on the skin side surface (the range 19) of the absorber 4 is preferably in the same range as the range in the longitudinal direction of the superabsorbent resin 18 arranged on the side edge portion of the absorber 4, for the purpose of absorbing water in a locality of discharge by the wearer such as in the vicinity of the urination opening portion, the superabsorbent resin 18 may be arranged in a smaller range such as only the range in the longitudinal direction corresponding to the urination opening portion.

Figure 6:
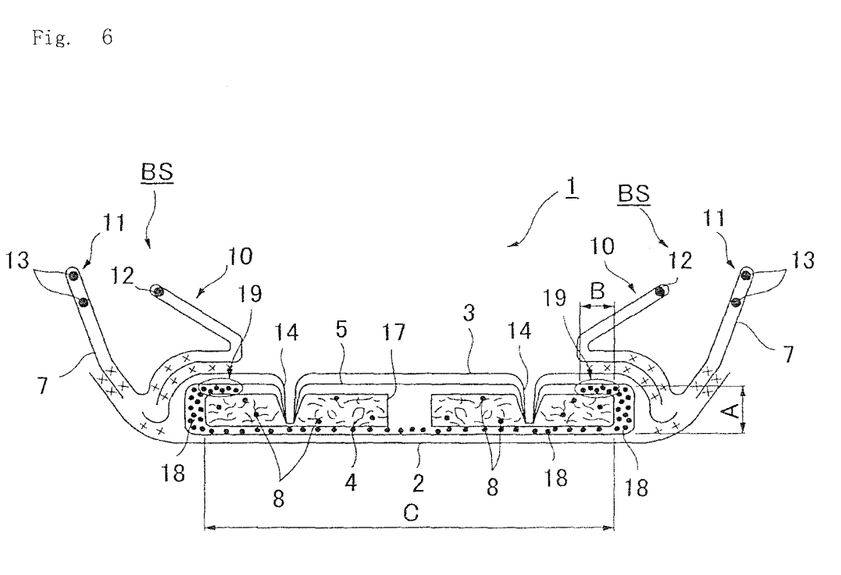
FIG. 6 is a vertical cross-sectional view (arrow view taken along line of FIG. 1) of the incontinence pad 1 showing yet another embodiment.

Furthermore, as shown in FIG. 6, the superabsorbent resin 18 may be arranged over the range in the longitudinal direction which is the surface on the non-skin side of the absorber 4 and which includes the body fluid inflow portion 17. In the surface on the non-skin side of the absorber 4, even when the superabsorbent resin 18 absorbs water to become swollen, since a grainy feel is not produced up to the skin side, the absorption capacity in the absorber 4 is increased without causing wearer discomfort. However, since the liquid-impermeable back surface sheet 2 may be damaged by the superabsorbent resin 18, a weight per unit area lower than the superabsorbent resin 18 arranged on the side edge portion of the absorber 4 is preferably provided.

Here, with respect to the range of the superabsorbent resin 18 dispersed to each portion, as shown in FIG. 6, the range (height) A of the superabsorbent resin 18 arranged on the side edge portion of the absorber 4 is substantially equal to the thickness of the absorber 4, and is set at 1 to 25 mm, is preferably set at 3 to 20 mm and is more preferably set at 7 to 15 mm. Moreover, the width B of the superabsorbent resin 18 arranged on the skin side surface of the absorber 4 is substantially equal to the width in which the side non-woven fabric 7 overlaps the absorber 4, and is set at 5 to 35 mm and is preferably set at 10 to 30 mm. Furthermore, the width C of the superabsorbent resin 18 arranged on the non-skin side surface of the absorber 4 is substantially equal to the width of the absorber 4, and is set at 60 to 200 mm and is preferably set at 70 to 180 mm.

Figure 7A:
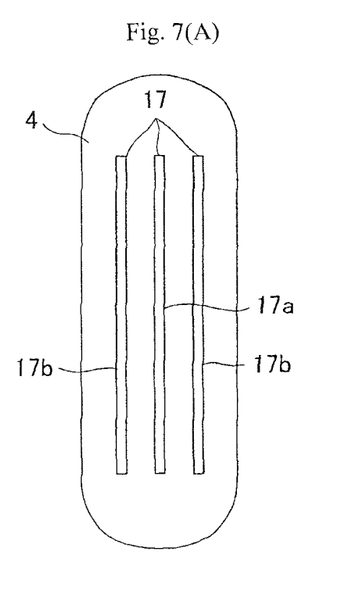
FIG. 7 is a plan view of the absorber 4 showing a body fluid inflow portion 17.
Figure 7B:
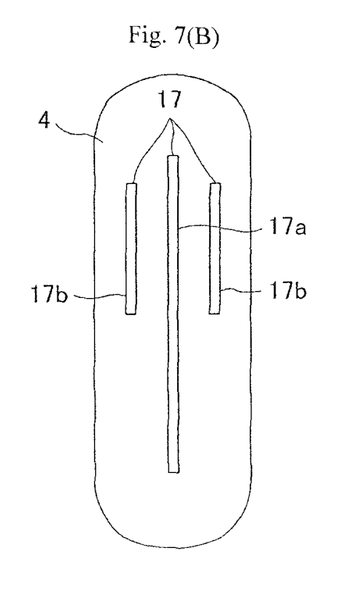

As shown in FIG. 1, one body fluid inflow portion 17 is provided along the longitudinal direction of the pad at least on the center line of the incontinence pad 1 substantially in the longitudinal direction in a range including the urination opening portion. As shown in FIG. 7(A), on each of both sides of a body fluid inflow portion 17a provided on the center line in the longitudinal direction of the pad, one or a plurality of body fluid inflow portions 17b, in the example shown in the figure, one body fluid inflow portion 17b is arranged, with the result that as a whole, a plurality of body fluid inflow portions 17, in the example shown in the figure, three body fluid inflow portions 17 may be provided. As shown in FIG. 7(B), the body fluid inflow portions 17b arranged on both sides in the width direction may be arranged only in the front side region of the pad including the urination opening portion of the wearer so as to receive a large amount of urine discharged, and in the back side region of the pad, the decrease in the absorption capacity may be reduced by providing the body fluid inflow portion 17.

Figure 8A:
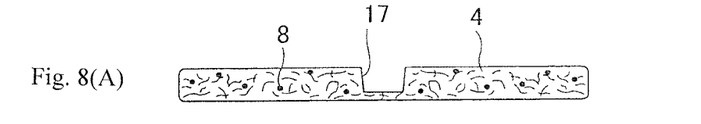
FIGS. 8(A) to 8(C) are vertical cross-sectional views of the absorber 4 showing a procedure for forming the body fluid inflow portion 17.
Figure 8B:
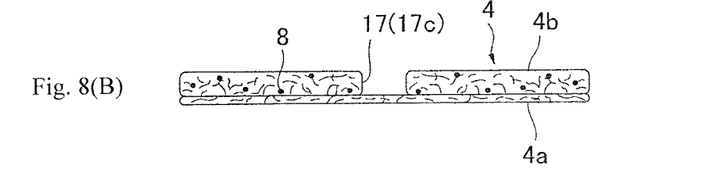
Figure 8C:
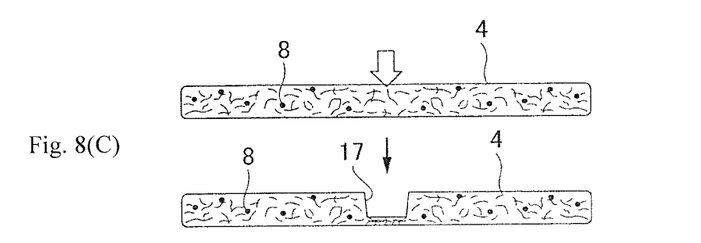

As shown in FIG. 2, the body fluid inflow portion 17 may be formed with an opening through which the absorber 4 penetrates from the skin side to the non-skin side and which has no bottom, and as shown in FIG. 8, the body fluid inflow portion 17 may be formed with a concave portion in which the absorber 4 is recessed from the skin side to the non-skin side and which has a bottom. When the body fluid inflow portion 17 is formed with the concave portion having the bottom, as shown in FIG. 8(A), a structure having the concave portion can be provided at the time of lamination, as shown in FIG. 8(B), on a lower layer absorber 4a serving as a bottom portion, an upper layer absorber 4b having an opening 17c can be laminated to form a multilayer structure and as shown in FIG. 8(C), an emboss can be added to use a means such as compression.

As shown in FIG. 2, the wrapping sheet 5 and the liquid-permeable front surface sheet 3 arranged on the skin side surface of the absorber 4 may be provided under tension on the skin surface side of the body fluid inflow portion 17 while being prevented from entering the concave groove of the body fluid inflow portion 17. In this way, body fluid passing through the liquid-permeable front surface sheet 3 and the wrapping sheet 5 easily flows into the body fluid inflow portion 17.

With respect to the dimensions of the body fluid inflow portion 17, the depth is equal to or more than 50% of the thickness of the absorber 4 and is preferably equal to or more than 80%, and the length in the longitudinal direction (i.e., lengthwise with respect to the pad) is 20 to 90% of the length of the absorber 4 in the longitudinal direction and is preferably 50 to 80%. The width is 5 to 50 mm and is preferably 10 to 30 mm. The body fluid inflow portion 17 may be formed so as to have a substantially uniform width in the longitudinal direction of the pad or may be formed such that different width dimensions are provided in the longitudinal direction of the pad such as in which only in the urination opening portion the width is relatively increased.

As the superabsorbent resin 18 arranged around the periphery of the absorber 4, the same one as the superabsorbent resin 8 mixed with the absorber 4 may be used or a superabsorbent resin having different physical properties may be used. For example, the superabsorbent resins may be so selected that the superabsorbent resin 8 mixed with the absorber 4 is higher in absorption speed than the superabsorbent resin 18 arranged around the periphery of the absorber 4 so that the rate of the diffusion of body fluid diffused within the absorber 4 is at a desirably high level, or the superabsorbent resins may be so selected that the superabsorbent resin 18 arranged around the periphery of the absorber is higher in the absorbed amount than the superabsorbent resin 8 mixed with the absorber 4 so that body fluid is blocked by the side edge portion of the absorber 4. The absorbencies referred to herein are at ambient atmospheric pressure ("normal pressure").

With respect to the weight per unit area of the pulp, the superabsorbent resin 8 and the superabsorbent resin 18, the weight per unit area of the pulp is 100 to 600 $g/m^2$ and is preferably 200 to 500 $g/m^2$, the weight per unit area of the superabsorbent resin 8 mixed with the absorber 4 is 150 to 500 $g/m^2$ and is preferably 200 to 450 $g/m^2$ and the mass ratio of the entire amount of polymer including the superabsorbent resin 18 is 30 to 80% and is preferably 40 to 70%. The weight per unit area of the superabsorbent resin 18 arranged around the periphery of the absorber 4 is 150 to 450 $g/m^2$ and is preferably 200 to 400 $g/m^2$ and the mass ratio of the entire amount of polymer including the superabsorbent resin 8 is 20 to 70% and is preferably 30 to 60%.

Although the thickness of the absorber 4 may be uniform as a whole, the end portions in the forward and backward direction with respect to the body fluid inflow portion 17 may be lower in thickness than the intermediate portion so that wearer comfort is enhanced.

In the incontinence pad 1, any one of the following, structures or a combination thereof can be adopted so that the wearer discomfort such as a grainy feel caused by the superabsorbent resin 18 arranged on the side edge portion of the absorber 4 is prevented. Firstly, the stereoscopic gathers BS are designed to have the double gather structure described previously or a loop-shaped hollow structure, and thus it is possible to realize a structure in which the side edge portion of the absorber 4 is prevented from making direct contact with the skin. Secondly, as the wrapping, sheet 5, a non-woven fabric having a large weight per unit area is used, and thus even when the side edge portion of the absorber 4 contacts the skin, wearer discomfort does not occur. Specifically, a non-woven fabric having about 15 to 25 $g/m^2$ is preferably result. Thirdly, as shown in FIG. 2, the side end of the liquid-permeable front surface sheet 3 external beyond the side end of the absorber 4, and is arranged so as to cover the superabsorbent resin 18. Fourthly, the side non-woven fabric 7 is formed in the shape of a double sheet or one having a large weight per unit area (about 20 to 35 $g/m^2$) is used.

Figure 9A:
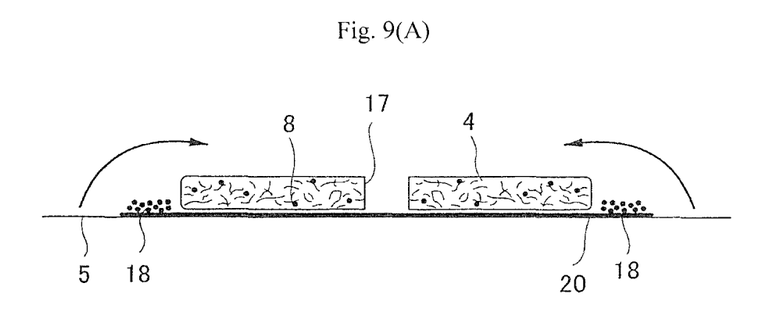
FIGS. 9(A), 9(B) are vertical cross-sectional views showing a procedure for fixing a superabsorbent resin 18.

Procedures for arranging the superabsorbent resin 18 on the side edge portion of the absorber 4 are described with reference to FIGS. 9(A) and 9(B). FIG. 9(A) shows a case where the superabsorbent resin 18 is fixed to the wrapping sheet 5. In this case, a hot-melt adhesive 20 whose width is wider than that of the absorber 4 is applied to the upper surface side of the wrapping sheet 5, in the center portion in the width direction on the upper surface side, the absorber 4 is laminated, thereafter a predetermined amount of superabsorbent resin 18 is dispersed to the portions on both sides of the absorber 4 to which the hot-melt adhesive 20 is applied and thus the wrapping sheet 5 is fixed. Thereafter, both side ends of the wrapping sheet 5 are folded so as to wrap the side edges of the absorber 4 (see FIG. 4).

Figure 9B:
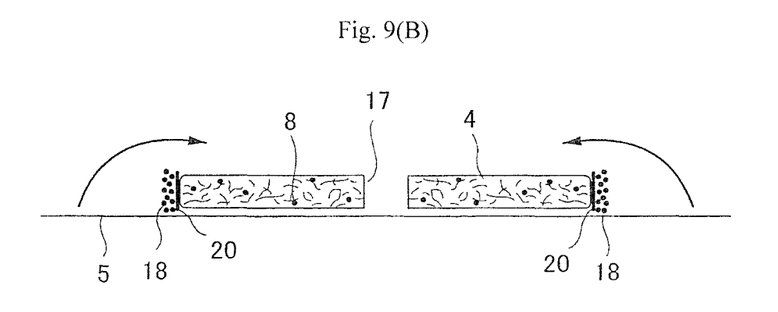

On the other hand, FIG. 9(B) shows a case where the superabsorbent resin 18 is fixed to the absorber 4. In this case, the lower surface of the absorber 4 is fixed to an approximate center portion of the wrapping sheet 5 by hot melt adhesive, and thereafter the hot-melt adhesive 20 is applied to the side edge portion of the absorber 4. A predetermined amount of superabsorbent resin 18 is dispersed to a predetermined range, and both side ends of the wrapping sheet 5 are folded so as to wrap the side edges of the absorber 4.

The superabsorbent resin 18 can be fixed to both side edge portions of the wrapping sheet 5 and the absorber 4, and in this case, the hot-melt adhesive 20 is applied to both side edge portions of the wrapping sheet 5 and the absorber 4.

In the case of the arrangement on the surface on the non-skin side of the absorber 4, before the absorber 2 is laminated on the wrapping sheet 5, the superabsorbent resin 18 is preferably dispersed to the wrapping sheet 5.

In the measurement of the weight per unit area, a sample is cut from each material with a roll cutter so as to have, a dimension of 20 mm×40 mm (±2 mm), and its weight is measured and is converted to a weight per 1 $m^2$ and is used as the weight per unit area.

In the measurement of the thickness, with a thickness measuring unit made by OZAKI MFG. Co., Ltd. (peacock, dial thickness gauge large type) model J-B (measurement range of 0 to 35 mm) or model K-4 (measurement range of 0 to 50 mm)), the measurement is performed with a measurement force of 3.0 N in a state were the sample and the thickness measuring unit are set horizontal.

Other Embodiment

In another embodiment, the lower surface side (the absorber side) of the liquid-permeable front surface sheet 3, a second sheet formed of hydrophilic non-woven fabric may be arranged between the liquid-permeable front surface sheet 3 and the absorber 4 so that the absorption speed of the body fluid is increased and the return of body fluid is prevented. The second sheet may be obtained by previously laminating the hydrophilic non-woven fabric integrally on the back surface of the liquid-permeable front surface sheet 3.

The invention claimed it:
1. An absorbent product comprising,
an absorber interposed between a liquid-permeable front surface sheet and a back surface sheet, and a side non-woven fabric arranged at each of left and right sides of the absorber on a skin side along a longitudinal direction of the absorbent product,
wherein the absorber includes only one concave groove-shaped body fluid inflow portion and said only concave groove-shaped body fluid inflow portion extends along the longitudinal direction of the absorbent product on a line which is at a center of a width of the absorbent product and over a range in the longitudinal direction including a body fluid discharge portion of a wearer of the absorbent product, and a granular powder superabsorbent resin is intensively provided at least on a side edge portion of the absorber and over the range in the longitudinal direction including the body fluid inflow portion, and
wherein the superabsorbent resin is not arranged on a surface of the skin side of the absorber in an entire zone in a width direction of the absorber between the side non-woven fabrics arranged at the left and right sides of the absorber, and the superabsorbent resin is intensively provided on a surface of the absorber on the skin side overlapping the side non-woven fabrics and over a range in the longitudinal direction including the body fluid inflow portion.

2. The absorbent product according to claim 1,
wherein the superabsorbent resin is arranged on a surface of the absorber on a non-skin side and over the range in the longitudinal direction including the body fluid inflow portion.

3. The absorbent product according to claim 1,
wherein the absorber is surrounded by a wrapping sheet, and
the superabsorbent resin is fixed either to both the absorber and the wrapping sheet or to one of the absorber and the wrapping sheet.

4. The absorbent product according to claim 1,
wherein the body fluid inflow portion is formed either with an opening through which the absorber penetrates from the skin side to the non-skin side or with a concave portion that is recessed from the skin side to the non-skin side and that has a bottom.

\* \* \* \* \*